United States Patent [19]

Pasqualucci et al.

[11] 3,933,801

[45] Jan. 20, 1976

[54] PROCESS FOR PREPARING RIFAMYCIN S BY HYDROLYSIS OF RIFAMYCIN O

[75] Inventors: Carmine Pasqualucci, Milan; Giuseppe Scarpitta, Pavia; Giovanni Bonfanti, Milan, all of Italy

[73] Assignee: Archifar Industrie Chimiche Del Trentino S.p.A., Rovereto, Italy

[22] Filed: Oct. 24, 1974

[21] Appl. No.: 517,834

[30] Foreign Application Priority Data
Nov. 29, 1973   Italy.................................. 31928/73

[52] U.S. Cl............................................ 260/239.3 P
[51] Int. Cl.$^2$................ C07D 515/20; C07D 515/10
[58] Field of Search............................. 260/239.3 P

[56] References Cited
FOREIGN PATENTS OR APPLICATIONS
924,472   4/1963   United Kingdom.......... 260/239.3 P

*Primary Examiner*—Henry R. Jiles
*Assistant Examiner*—Robert T. Bond
*Attorney, Agent, or Firm*—Waters, Schwartz & Nissen

[57] ABSTRACT

A process for preparing rifamycin S from rifamycin O. Rifamycin O is dissolved in a mixture of an organic solvent and an alcohol at room temperature. The rifamycin O is then hydrolyzed with a mineral acid and the thus obtained rifamycin S is purified by crystallization.

4 Claims, No Drawings

PROCESS FOR PREPARING RIFAMYCIN S BY HYDROLYSIS OF RIFAMYCIN O

This invention relates to a process for preparing rifamycin S by hydrolysis of rifamycin O.

It is known that rifamycin S is a substance of the rifamycin class constituting an intermediate for preparing highly active derivatives (antibiotics) and used in the pharmaceutical field, such as rifampicin and rifamycin SV. Heretofore, for the preparation of rifamycin S use was made of the method as disclosed in the British Pat. Specification No. 924,472, according to which rifamycin S is obtained from rifamycin O by removal of a glycol group through hydrolysis and the thus formed rifamycin S is then isolated by a suitable treatment.

According to the method disclosed in the mentioned patent, the hydrolysis is carried out in homogenous phase in a mixture comprising water, mineral acids and a water miscible solvent, such as methanol or acetone.

The described process exhibits serious disadvantages. Thus, under the conditions described in the patent mentioned, owing to poor solubility of rifamycin O in mixtures comprising water miscible solvents, the reaction can be carried out only at low concentrations. Additionally, due to phase homogeinity, both the amount of acid and the hydrolysis temperature are critical since the rifamycins degrade when in contact with the strong acids in the presence of water miscible solvents. This is illustrated in the British patent when the hydrolysis is carried out either at pH 3 at room temperature (in which case the reaction time is 4 days), or the hydrolysis is carried out with an amount of acid which is about 25 times by weight greater than the antibiotic (and in this case low temperatures are required to restrict degradation and the reaction time is reduced to about 8 hours).

It is the primary object of the present invention to provide a process for preparing rifamycin S which can be carried out by hydrolizing rifamycin O at high concentrations while using greatly reduced amounts of reaction acid.

It is another object of the invention to provide a process for preparing rifamycin S in a very easy manner and in very short times.

These and other objects are achieved by a process wherein rifamycin O at a concentration higher than 60,000γ/ml is dissolved in a mixture of a water immiscible chlorinated organic solvent and a water miscible alcohol at a temperature in the range of about 0°–30°C, adding a strong mineral acid in a ratio of about 1/10–1.5/1 by weight relative to the amount of treated rifamycin O, hydrolyzing the rifamycin O in heterogeneous phase and while thoroughly stirring the reaction mass for a time ranging from about 40 minutes to about 3.5 hours. The reaction mass is washed at least once with aqueous media and then vacuum concentrated to dryness, the solid product obtained being then taken up with a water miscible alcohol and finally cooled to crystallize rifamycin S.

It is important to note that the use of a water immiscible solvent along with an alcohol affords a high solubility for rifamycin O, whereby the process can be carried out at high concentrations of this rifamycin. Moreover, the presence of the water immiscible solvent causes hydrolysis to occur in a heterogeneous phase which, while requiring a thorough stirring of the liquid media, has the advantage of a negligible antibiotic degradation.

The invention can be more clearly understood with reference to the following examples which are illustrative and not limitative of the invention.

EXAMPLE 1

45 Grams of rifamycin O were dissolved in a mixture of $CH_2Cl_2$: methanol (ratio 1:1) at a concentration of 70,000γ/ml and at 18°C. 42 grams of concentrated HCl were then slowly added in 30 minutes, still at a constant temperature of 18°C.

Stirring was maintained for 1 hour 20 minutes, as required for hydrolysis to occur.

The organic solution was then washed for 3 times with 30 ml portions of aqeous media, the first of which comprised a saturated solution of sodium bicarbonate. This organic phase was then vacuum concentrated to dryness. The mass was taken up with 45 ml isopropyl alcohol and cooled thus precipitating rifamycin S which was collected by filtering and then vacuum dried. 36 g rifamycin S having a spectrophotometric titer of 98% were obtained.

EXAMPLE 2

50 Grams of rifamycin O were dissolved in a mixture of 3:1 $CHCl_3$-ethanol at a concentration of 80,000γ/ml and at a temperature of 10°C.

Still at 10°C, 20 grams of concentrated $H_3PO_4$ were then slowly added in 30 minutes. Stirring was continued for 3¼ hours as required for hydrolysis completion. The organic phase was washed 3 times, with 350 ml portions of with aqueous media and then vacuum concentrated to dryness. The mass was taken up with 50 ml of isopropanol and cooled, thus precipitating 41 grams of rifamycin S having a spectrophotometric titer of 97.9%.

EXAMPLE 3

45 Grams of rifamycin O were dissolved in a mixture of 1:1 $ClCH_2CH_2Cl$-propanol at a concentration of 65,000γ/ml and at a temperature of 20°C. 47 grams of concentrated HCl were slowly added in 30 minutes, with the temperature maintained always at a constant level.

Stirring was continued for 1¼ hours, as required for hydrolysis completion. The organic phase was washed 3 times with 300 ml portions of water, the first wash being sligthly basic due to the presence of sodium bicarbonate, and then vacuum concentrated to dryness.

The product was taken up with 50 ml of absolute ethanol and cooled, thus precipitating 35 grams of rifamycin S spectrophometric titer of 98%.

EXAMPLE 4

45 Grams rifamycin O were dissolved in a mixture of 4:1 $CHCl_3$-methanol at a concentration of 90,000γ/ml and at a temperature of 30°C.

15 Grams of 98% $H_2SO_4$ were slowly added dropwise and the product completely hydrolized in 45 minutes.

The organic phase was portionally washed with water, vacuum concentrated to dryness, taken up with absolute ethanol and cooled, thus precipitating 25 grams of rifamycin S having a spectrophotometric titer of 98%.

EXAMPLE 5

45 Grams of rifamycin O were dissolved in a mixture of 1:1.5 $CCl_4$-propanol at a concentration of 85,000γ/ml and at a temperature of 30°C.

A mixture of 1:1 $H_2SO_4$—$H_2O$ was slowly added dropwise in an amount of 50 grams of and the reaction now was stirred for 3 hours.

Upon hydrolysis completion, the organic phase was portionally washed with water, vacuum concentrated, taken up with absolute ethanol and cooled, thus precipitating 29 grams of rifamycin S having a spectrophotometric titer of 97%.

By the process according to the present invention, such as shown in the above disclosed examples, a hydrolysis of rifamycin O is provided having the following advantages over the prior art processes:

a. High concentration of the antibiotic can be reacted, thus using equipment of a much reduced size and far lower amounts of solvent can be used in comparison to the prior art;

b. An amount of acid related to the antibiotic of about 1/100 that of the prior art reactions can be used;

c. Rifamycin stability is achieved during hydrolysis and hence almost quantitative recoveries of product are obtained, no particular caution having to be observed in the course of reaction, unlike the case of the prior art; and d. Substantially lower reaction times than those occuring with the prior art processes, and temperatures ranging from 0°C to 30°C can be used.

What we claim is:

1. A process for preparing a rifamycin S comprising the steps of dissolving rifamycin O at a concentration higher than 60,000γ/ml in a mixture of a water immiscible chlorinated organic solvent and a water miscible alcohol at a temperature in the range of about 0°–30°C and which mixture forms a heterogeneous phase, adding a strong mineral acid in a ratio of about 1:10–1.5:1 by weight to the amount of treated rifamycin O to the mixture then hydrolyzing said rifamycin O in said heterogeneous phase while thoroughly stirring the reaction mass for a time in the range of about 40 minutes to about 3.5 hours and at a temperature in the above range, washing the reaction mass with water and then vacuum concentrating the reaction mass to dryness, the solid obtained then being taken up with a water miscible alcohol, and finally cooling to crystallize rifamycin S.

2. A process as set forth in claim 1 wherein the temperature at which the hydrolysis of the rifamycin O is carried out is in the range of about 18°–20°C.

3. A process as set forth in claim 1 wherein the strong mineral acid is added in a same amount by weight as the rifamycin O being treated in the process.

4. A process as set forth in claim 1 wherein the reaction mass is washed with slightly basic water.

* * * * *